(12) United States Patent
Stanley et al.

(10) Patent No.: US 8,311,854 B1
(45) Date of Patent: Nov. 13, 2012

(54) MEDICAL QUALITY PERFORMANCE MEASUREMENT REPORTING FACILITATOR

(75) Inventors: Rex Allen Stanley, Montgomery, AL (US); Janice Elaine Powell, Tallahassee, FL (US); Francis Paul Robles, Jr., Tallahassee, FL (US)

(73) Assignees: Unicor Medical, Inc., Montgomery, AL (US); Megas, LLC, Tallahassee, FL (US)

( * ) Notice: Subject to any disclaimer, the term of this patent is extended or adjusted under 35 U.S.C. 154(b) by 349 days.

(21) Appl. No.: 12/494,697

(22) Filed: Jun. 30, 2009

Related U.S. Application Data

(60) Provisional application No. 61/077,370, filed on Jul. 1, 2008.

(51) Int. Cl.
*G06F 19/00* (2011.01)

(52) U.S. Cl. .......................................................... 705/3

(58) Field of Classification Search .................... 705/2, 3
See application file for complete search history.

(56) References Cited

U.S. PATENT DOCUMENTS

| | | | |
|---|---|---|---|
| 5,544,044 A | 8/1996 | Leatherman | |
| 5,953,704 A | 9/1999 | McIlroy et al. | |
| 6,370,511 B1 | 4/2002 | Dang | |
| 6,542,905 B1 * | 4/2003 | Fogel et al. | 1/1 |
| 6,658,431 B1 | 12/2003 | Norman, Jr. | |
| 6,770,029 B2 | 8/2004 | Iliff | |
| 7,464,041 B2 | 12/2008 | Merkin et al. | |
| 2002/0111826 A1 | 8/2002 | Potter et al. | |
| 2002/0123670 A1 | 9/2002 | Goetzke et al. | |
| 2003/0149597 A1 | 8/2003 | Zaleski | |
| 2004/0254816 A1 | 12/2004 | Myers | |
| 2005/0065816 A1 | 3/2005 | Limberg et al. | |
| 2005/0216312 A1 | 9/2005 | Bellin et al. | |
| 2006/0020492 A1 | 1/2006 | Cousineau et al. | |
| 2006/0161456 A1 | 7/2006 | Baker et al. | |
| 2006/0265253 A1 * | 11/2006 | Rao et al. | 705/3 |
| 2007/0214013 A1 | 9/2007 | Silverman | |
| 2008/0154642 A1 * | 6/2008 | Marble et al. | 705/3 |
| 2008/0215370 A1 | 9/2008 | Dent et al. | |
| 2009/0076841 A1 * | 3/2009 | Baker et al. | 705/2 |
| 2009/0164249 A1 * | 6/2009 | Hunt et al. | 705/3 |

FOREIGN PATENT DOCUMENTS

| | | |
|---|---|---|
| WO | 03036542 A3 | 5/2003 |
| WO | 2008103749 A1 | 8/2008 |

OTHER PUBLICATIONS

CMS, Quality Measures Management Information System (QMIS), http://www.cms.hhs.gov/apps/QMIS/Default.asp.
Iezzoni, Assessing Quality Using Administrative Data, Annals of Internal Medicine, 127(5)(2):666-674 (Oct. 15, 1997).
CMS, PQRI Tool Kit, http://www.cms.hhs.gov/PQRI/31_PQRIToolkit.asp.

\* cited by examiner

*Primary Examiner* — John Pauls
(74) *Attorney, Agent, or Firm* — Dennis JM Donahue, III; CreatiVenture Law, LLC

(57) ABSTRACT

A system and process evaluate the presence and absence of particular quality measure codes in a set of patient records and provide a medical service provider with options for taking corrective action when a quality measure code that should be in a patient's record is missing. Patient records are selected based on specific medical condition code combinations along with specifications with age and gender criteria. A quality measure identifier uniquely identifies a set of specification criteria, medical condition criteria, and quality measure criteria.

20 Claims, 9 Drawing Sheets

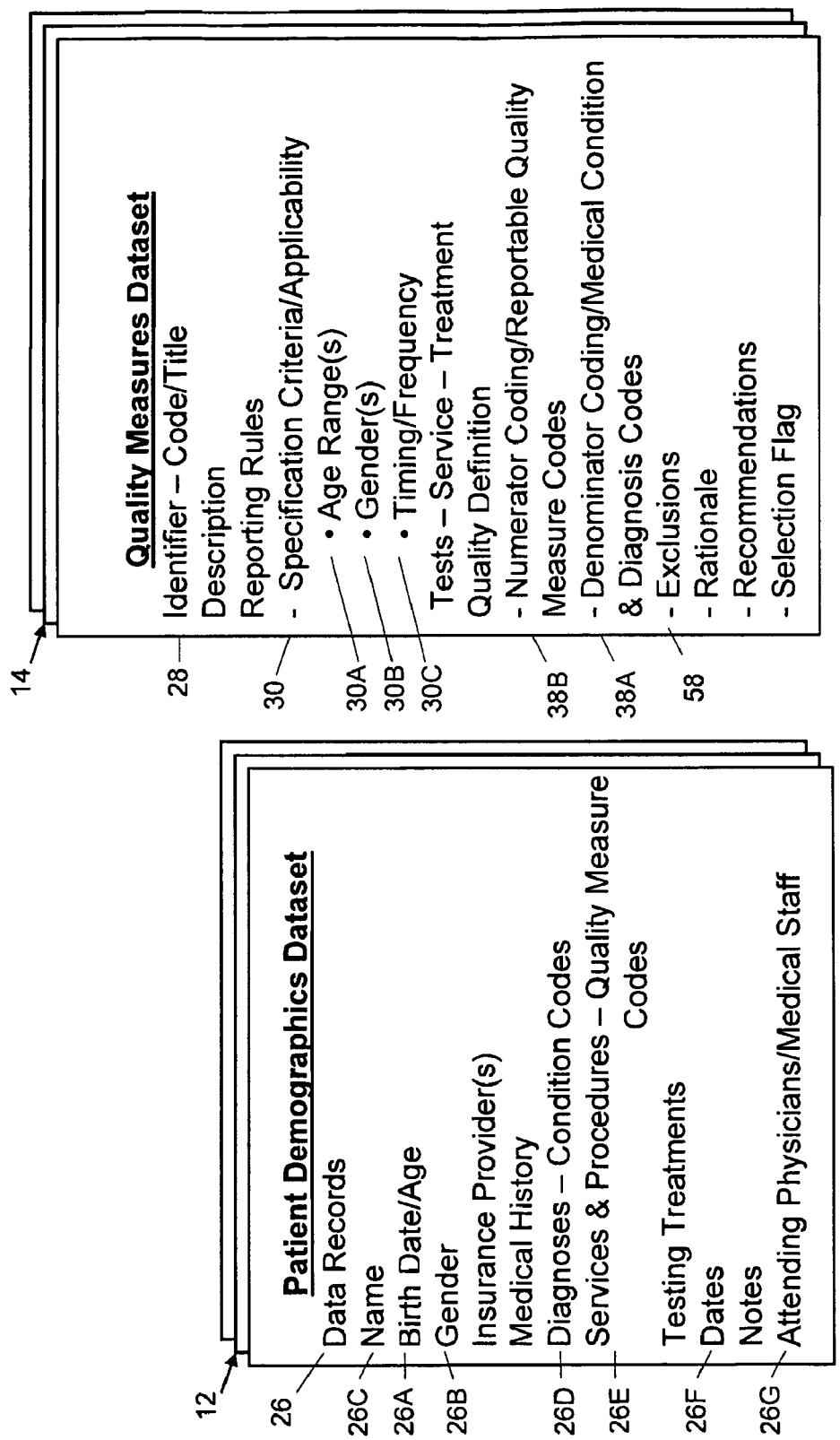

Figure 4A

Patient Information ← 32

| Name | Birth Date | Insurance |
|---|---|---|
| | OM OF | |

| Date | Summary/Notes | Code(s) | Physician |
|---|---|---|---|
| | | | |
| | | | |
| | | | |

Figure 4B

| No. | Edit Name | Category | Blue Shield | Tricare | Other | Medicaid | Medicare |
|---|---|---|---|---|---|---|---|
| 1178 | PQRI- Vascular Access for Patients Undergoing Hemodialysis | PQRI | ☐☐☐☐☐ | ☐☐☐☐☐ | ☐☐☐☐☐ | ☐☐☐☐☐ | ☐☐☒☒☐ |
| 1179 | PQRI- Influenza Vaccination in Patients with End State {... | PQRI | | | | | |
| 1180 | PQRI- Plan of Care for ESRD Patients with Anemia | PQRI | | | | | |
| 1181 | PQRI- Plan of Care for Inadequate Hemodialysis in ESRD Patients | PQRI | | | | | |
| 1182 | PQRI- Plan of Care for Inadequate Peritoneal Dialysis | PQRI | | | | | |
| 1183 | PQRI- Testing of Patients with Chronic Hepatitis C (HCV) for ... | PQRI | | | | | |
| 1184 | PQRI- Initial Hepatitis C RNA Testing | PQRI | | | | | |

The edit determines if the PQRI measure has been reported

[Save] [Refresh] [Exit]

| Claim ID | Patient Account | Patient Name | Provider | Payer | Billed Amount |
|---|---|---|---|---|---|
| 0000001 | PQRI_1101_A | NAME | DOCTOR | Medicare [62310] MEDICARE | $140.50 |

| | | |
|---|---|---|
| 21014 | (PROV) The billing provider NPI is either missing, contains invalid characters or is malformed. The billing provider NPI is required. Claim Data: Billing NPI = | Reject Claim |
| 21015 | (PROV) The rendering provider NPI is either missing, contains invalid characters or is malformed. The Rendering provider NPI is required. Claim Data: Rendering NPI = 234567893 | Reject Claim |
| 1101 | (PQRI) PQRI Measure = 1 (Hemoglobin A1c Poor Control in Type 1 or 2 Diabetes Mellitus). Reporting requirements have not been met. Allowing Reporting Codes: 3044F, 3045F, 3046F | Informational Message |
| 1102 | (PQRI) PQRI Measure = 2 (Low Density Lipoprotein Control in Type 1 or 2 Diabetes Mellitus). Reporting requirements have not been met. Allowed Reporting Codes: 3048F, 3049F, 3050F | Informational Message |
| 1103 | (PQRI) PQRI Measure = 2 (Low Density Lipoprotein Control in Type 1 or 2 Diabetes Mellitus). Reporting requirements have not been met. Allowed Reporting Codes: 2000F, 3074F, 3075F, 3077F and 3078F, 3080F | Informational Message |

| Seq. | Service Date | POS | CPT Code | Modifiers | Diagnoses | Billed | Error |
|---|---|---|---|---|---|---|---|
| 01 | 01-01-2008 | 11 | G0270 | | 250.00 | $140.50 | |

G0270 MEDICAL NUTRITION THEREAPY; REASSESSMENT AND SUBSEQUENT INTERVENTION(S) FOLLOWING SECOND REFERRAL IN SAME YEAR FOR CHAGNE IN DIAGNOSIS, MEDICAL CONDITION OR THREATMENT REGIMENT (INCLUDING ADDITIONAL HOURS NEEDED FOR RENEWAL DISEASE), FACE TO FACE WITH THE PATIENT EACH 15 MINUTES

Figure 4C

MEDICAL QUALITY PERFORMANCE MEASUREMENT REPORTING FACILITATOR

CROSS-REFERENCE TO RELATED APPLICATIONS

This application claims priority from U.S. Provisional Patent Application No. 61/077,370 filed Jul. 1, 2008.

BACKGROUND OF THE INVENTION

1. Field of the Invention

This invention relates to computerized practice management systems for doctors' offices and other medical service providers in providing services to their patients, and is particularly related to the use of these systems for tracking the medical care being provided to the patients and reporting quality of care results to the patients' insurance providers.

2. Related Art

The 2004 Current Procedural Terminology (CPT) book produced by the American Medical Association included a new category of CPT codes, Category II Codes. These codes were intended to facilitate data collection about the quality of care rendered by coding certain services and test results that support nationally established performance measures and have an evidence base as contributing to quality of patient care. These codes describe clinical components that may be included in evaluation and management services or other clinical services and therefore do not have a direct monetary values associated with them. Category II codes may also describe laboratory test results, medicines being prescribed and procedures intended to address patient safety practices, or services reflecting compliance with state or federal law. The AMA has updated, added to and amended this code set biannually since 2004. It would be expected that the number of codes and services described will continue to increase in the foreseeable future. CPT is a registered mark of the American Medical Association, and the CPT codes are widely used in the medical field with other medical procedural codes, including quality measure codes and corresponding medical nomenclature for tracking and reporting medical procedures and services, including CPT Category I and now CPT Category III.

The Tax Relief and Health Care Act of 2006 (TRHCA) authorizes a physician quality reporting system. This performance measurement program, which the Centers for Medicare & Medicaid Services (CMS) named "Physician Quality Reporting Initiative" (PQRI), was implemented on Jul. 1, 2007. The TRHCA specifically authorized, and established provisions for implementation of, bonus payments for satisfactory submission of data on the quality of covered professional services furnished to Medicare beneficiaries.

The PQRI program is defined by a matrix of quality measures developed by CMS. In general, the quality measures consist of a numerator and a denominator that permit the calculation of the percentage of a defined patient population that receive a particular process of care or achieve a particular outcome. The denominator population is defined by certain ICD-9 and CPT Category I codes (medical condition codes generally) specified in the measure that are submitted as part of a claim for Medicare Physician Fee Schedule services by eligible professionals. The International Classification of Diseases, 9th Revision (ICD-9) is maintained jointly by the National Center for Health Statistics (NCHS) and the Centers for Medicare & Medicaid Services (CMS). If the specified denominator codes for a measure are not included in the patient's claim as submitted, then the patient does not fall into the denominator population, and the PQRI measure does not apply to the patient. For patients that are included in the denominator population, the applicable CPT Category II code (or other quality measure codes, such as the temporary HCPCS G code where CPT Category II codes are not yet available) that defines the numerator should be submitted. Where a patient falls in the denominator population but specifications define circumstances in which a patient may be excluded from the measure's denominator population, CPT Category II code modifiers 1-P, 2-P, or 3-P are available to describe medical, patient, or system reasons, respectively, for such exclusion. In situations for which exclusions do not apply, the CPT Category II modifier 8-P may be used to indicate that the process of care was not provided for a reason not otherwise specified.

To successfully report quality data for a measure under the PQRI program, a quality measure code (CPT Category II code or G code) must be reported for a numerator match with the denominator population, with or without an applicable CPT Category II code modifier (1-P, 2-P, 3-P, or 8-P). Instructions specific to each measure provide additional reporting information. Instructions for some measures limit the frequency of reporting necessary in certain circumstances, such as for patients with chronic illness for whom a particular process of care is provided only periodically. The measure specifications are organized to provide the information in a standardized format, having a Measure Title, Measure Description, Instructions on Reporting (frequency, timeframes, and applicability), Numerator Coding, Definitions of Terms, Coding Instructions, CPT Category II Exclusion Modifiers, Denominator Coding, Rationale Statement and Clinical Recommendations. Examples of quality reporting measure criteria are available through the CMS web site (www.cms.hhs.gov/apps/QMIS/browseMeasures.asp).

Providers currently have an option to participate or not participate in the PQRI program. However many people believe that at some future point CMS may make this a mandatory program. It is also quite possible that many private insurance companies may adapt the PQRI or some other pay for performance model based on the same or similar quality measures. These performance measurement programs may be either optional or mandatory.

There are several difficulties that providers and their staff face in participating in performance measurement programs. First, not all of the quality measures are appropriate for all patients. Appropriateness may be bases on any combination of diagnoses, procedures and tests performed, age and sex of patient. Also, not all of the quality measures are appropriate to all practices, and the physician and staff must decide which measures are appropriate to their practice and their patients and also choose the measures for which they expect to participate in the program. Once the decision is made on the measures for participation, the information must be communicated to all of the members in the healthcare team who are involved in providing, ordering, documenting or reporting appropriate services. Due to the large number of patients seen by providers and the number of measures which are available, keeping track of what services to provide and report can be very difficult for the providers and staff.

Additionally, Medicare's program is designed to allow the provider to participate in the program and send in the quality measure data with their claims. However, in order to receive any bonus, the provider must report on a minimal percentage of all patients that qualify for a particular quality measure which results in bonus payments being an all or nothing proposition. Therefore, if a provider or a member of the healthcare staff forgets to report the appropriate data even one time, it could mean the difference in whether the provider receives a significant payment or receives nothing.

CMS created the 2007 Physician Quality Reporting Initiative (PQRI), which establishes a financial incentive for eligible professionals to participate in a voluntary quality-reporting program. Eligible professionals who successfully report a designated set of quality measures on claims for dates of service during a set period of time may earn a bonus payment of total allowed charges for covered Medicare physician fee schedule services during that same period. CMS Specifications for reporting the quality measures are defined on the CMS PQRI website (http://www.cms.hhs.gov/pqri). In 2007, PQRI reporting was based on seventy-four (74) unique measures and continues to grow in scope.

On its web site, CMS provides a PQRI "Tool Kit" to help healthcare professionals use PQRI measurements and reporting in their respective medical practices (www.cms.hhs.gov/PQRI/31_PQRIToolkit.asp). However, the PQRI "Tool Kit" is a manual system that is not integrated into the computerized practice management systems that are used by many healthcare professionals and there is no recommendation or other suggestion on how the manual system may be automated or incorporated into computerized practice management systems. Although the PQRI Tool Kit allows providers to download files which contain work sheets to assist in (1) deciding which of the quality measures they might participate in, (2) identifying patients who meet the qualifications for reporting, and (3) assisting in the decisions of what data and level II codes to report, the lack of automation leaves the provider and staff with the additional problems of remembering the measures for which they have chosen to participate in the program, remembering the required services and making sure the necessary data is reported, and communicating all of the relevant information to the appropriate office staff for the medical practice.

Accordingly, the prior systems and resources are paper-driven, manual operations which require the provider to remember the measures, patients and requirements needed to be reported as well as ensuring that the information is reported. With hundreds of requirements that can change over time and may vary depending on combinations of diagnoses, patient age and gender, and procedures and tests performed, it is an overwhelming task to manually manage the information. Accordingly, there remains a need for assisting providers with an automated tool to manage the information and provide a knowledge-based process for managing the care of patients and the reporting of the care to the patients' insurance providers.

SUMMARY OF THE INVENTION

The present invention is an automated computer system and processes for managing the care of patients and providing the patients' insurance providers with reports on the quality of the medical care. The computer-based system incorporates the quality measures and corresponding patient information in database records, queries the database for a presenting patient and selects the matching results, thereby ensuring that the proper actions are taken and are reported appropriately. Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

The present invention assists medical providers in ensuring the proper information is included in reports required by performance measurement programs, allowing the providers to increase income, decrease personal time and staff time spent on these programs. The present invention also results in a decrease in reporting errors. The ability of providers to provide government offices and private insurance carriers with correct data allows them to use the data in programs intended to result in an overall improvement in the quality of medical care.

BRIEF DESCRIPTION OF THE DRAWINGS

The present invention will become more fully understood from the detailed description and the accompanying drawings, wherein:

FIG. 2 is a diagram of a patient demographics dataset;

FIG. 3 is a diagram of a quality measures dataset;

FIGS. 4A-4C are screen shots of user interface displays;

DETAILED DESCRIPTION OF THE PREFERRED EMBODIMENTS

Figure 1:
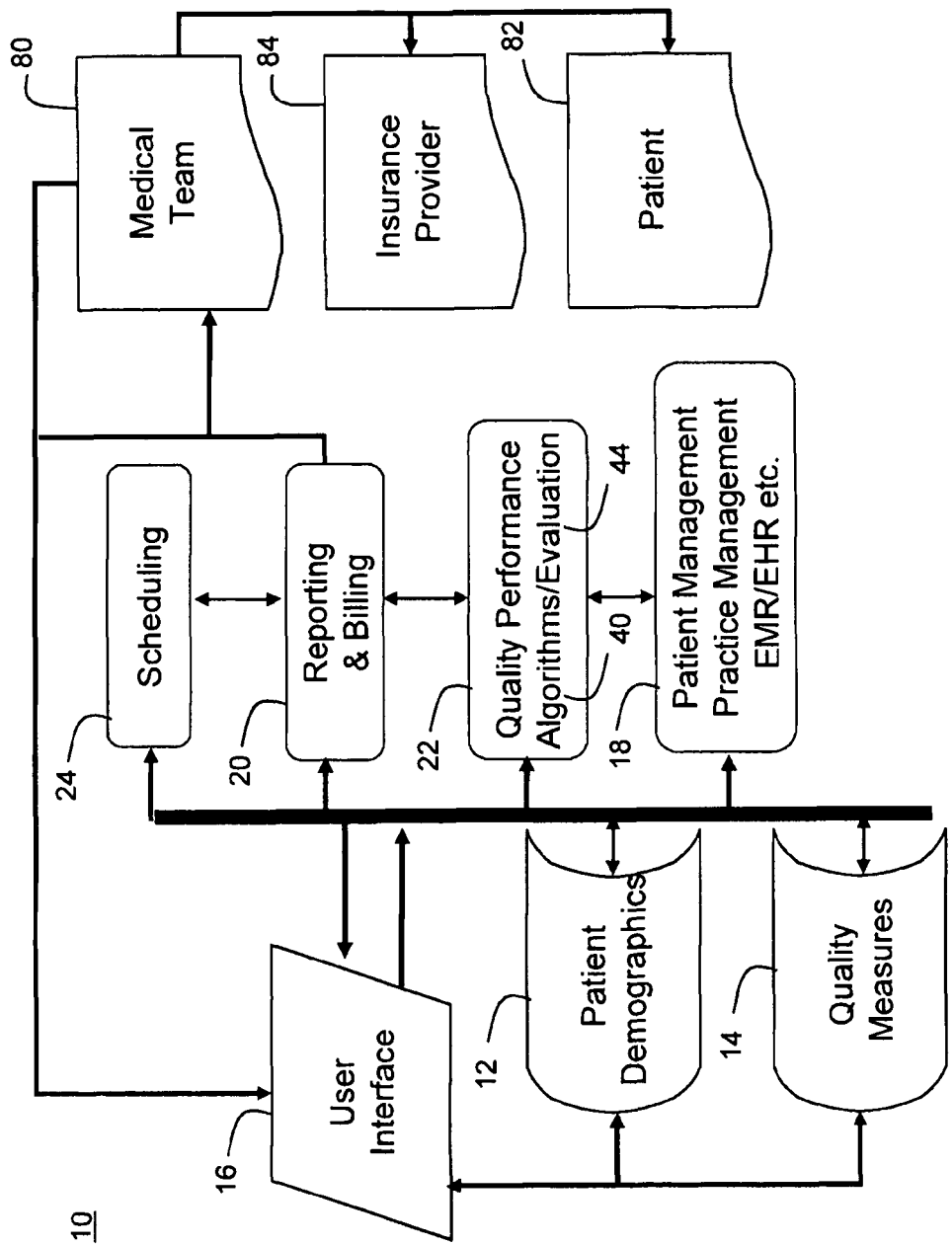
FIG. 1 is a block diagram of the modules of a practice management system according to the present invention.

The present invention is an automated computer system 10 and corresponding processes 100 for a team of medical service providers 80 to manage the care of patients 82 and reporting the quality of the care to the patients' insurance providers 84. Specifically, physicians, other healthcare providers and their respective staffs use the automated computer system to manage the care of the patients 82 and report appropriately performance measurement programs to the insurance providers 84. The automated system of the present invention accounts for variations in reporting requirements that may be set by different insurance providers.

As illustrated in FIGS. 1-4, the quality medical care system 10 has a quality performance module 22 which evaluates a set of specified data records 36 for the presence or absence of quality measure codes 26E that correspond with a particular set of reportable quality measure codes 38B. As discussed in detail below, the system 10 selects the specified data records 36 and the set of reportable quality measure codes 38 based on a quality measure identifier 28 which is chosen by the medical service provider 80. When one of the specified data records 36 does not have a match between its quality measure codes 26E and the reportable quality measure codes 38, the system 10 determines a quality measure error code 42A for the medical service provider 80 to take a corrective action 52 to resolve the error defined by the error code. To determine the appropriate corrective action based on the error code, the patient's chart and other records can be reviewed by the medical staff, and in a situation where a medical procedure was already performed but a particular quality measure code 26E was not entered into a patient's data record 26, the mandated quality measure code 60 can be added before the specified data records 36 are reported to the insurance provider 84. Alternatively, the medical staff may schedule an appointment or tests for the patient in a situation where a mandated medical procedure 62 needs to be performed so that the corresponding quality measure code 26E can be entered into the patient's data record 26 and properly reported to the patient's insurance provider 84.

In one embodiment of the invention, the quality medical care system 10 functions by storing information in one or more databases, such as information regarding the patients 82 and their care in a demographics dataset 12 and information regarding quality measures in a quality measure dataset 14. The medical service provider 80 interacts with the quality medical care system 10 through a user interface 16. As with current practice management systems, the user interface 16 is in operable communication with the datasets 12, 14 as well as a practice management module 18. Using patient information data fields 32 on the user interface 16, the medical service provider 80 can enter and update the data records 26 on the patients 82, update the information in the quality measure dataset 14, and perform other administrative tasks that are basic to most practice management systems, such as scheduling patient appointments and generating bills and other reports. Accordingly, as with current practice management systems, the practice management module 18 also communicates with a reporting module 20 and a scheduling module 24.

The selection of the specified data records 36 for the quality measurement evaluation 44 begins with the user selecting a defined quality measure identifier 28A from the quality measure identifiers 28 listed on the selection screen 34. The defined quality measure identifier 28A correlates to a unique combination of specification criteria 30, medical condition criteria 38A and reportable quality measure codes 38B. The specification criteria 30 preferably include age criteria 30A, gender criteria 30B, and date criteria 30D. The system 10 can store those quality measure identifiers 28 that for which the medical service provider 80 chooses to and can provide a flag 50 through the user interface 16 to remind the appropriate medical staff.

Figure 6:
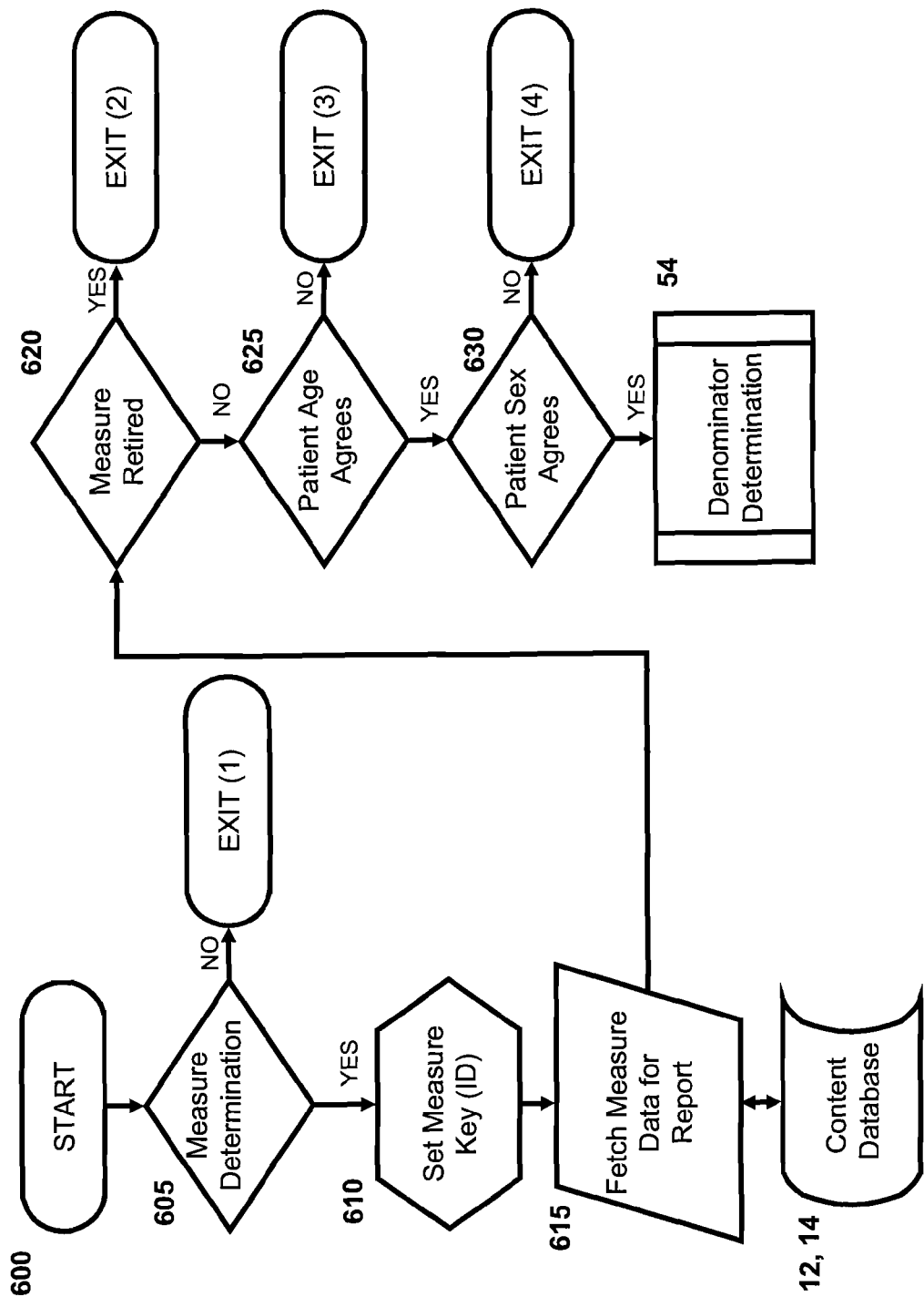
FIGS. 6A-6C are flow charts of the process operations.

The practice management module 18 or the quality performance module 22 determines the specified data records 36 by matching biographical information 26A, 26B in the data records 26 of the patients with the particular specification criteria 30 of the defined quality measure identifier 28A. Preferably, the date criteria 30D is also used to limit a range of dates so that data records with retired measures 620 (FIG. 6A, discussed below) are not included in the quality measurement evaluation 44; the corresponding dates 26F should be entered into the data records 26 with the quality measure codes 26E for the medical services that have been performed. Also, when the reportable quality measure codes 38B or other aspects of the quality measurement evaluation 44 differ for various insurance providers 84A-84E, the data records 26 can also include an insurance code 84A which can be matched with those quality measure identifiers 28 that are used by the respective insurance providers. Additionally, since reporting of the quality measures can be performed for individual physicians as well an entire medical practice, the data records 26 can also include information on the attending physician 26G.

Some quality measures 14 may also include exclusion criteria 58 for those patients whose biographical information and medical condition would otherwise qualify their data records 26 for inclusion in the specified data records 36. The exclusion criteria 58 can include particular codes or code modifiers to identify medical, patient, or system reasons, respectively, for the exclusion of data records 26 from the specified data records 36, i.e., excluding certain patients 82 from the denominator population 54A. When the practice management module 18 determines the specified data records 36 for the defined quality measure identifier 28A, they are communicated to the quality performance module 22.

The quality performance module 22 uses algorithms 40 for the evaluation 44 of the specified data records 36 which cross-reference the quality measure codes 26E in the specified data records 36 with the reportable quality measure codes 38B. As discussed below with reference to Tables I & II below, there does not need to be a one-to-one relationship between the reportable quality measure codes 38B and the quality measure codes 26E in the specified data records 36. There may be several quality measure codes 26E that can satisfy any one of a number of alternative reportable quality measure codes 38B. Generally, the algorithms 40 for the evaluation 44 include the measure determination for the specified data records 36 as described above as well as a denominator determination 54 and a numerator determination 56. The particular processes for these determinations are explained below with reference to FIGS. 5 and 6. In general, the denominator determination 54 produces a denominator population 54A by selecting the specified data records 36 which include medical condition codes 26D that are equivalent to the medical condition criteria 38A, and the numerator determination 56 is a numerator match 56A of the quality measure codes 26E in the specified data records 36 with the reportable quality measure codes 38B.

When the quality performance module 22 determines that there is an inconsistency between the data records for a patient and the reporting requirements, the quality measure error code 42A is determined from a set of error codes 42. As discussed above, to remove the inconsistency and resolve the error, the error code 42A corresponds with a notice 48 on certain actions that can be taken in the medical practice. In the situation where a medical procedure needs to be performed so that it can be reported, the medical staff can enter a scheduling notice with the mandated medical procedure to the scheduling module through the user interface so that the procedure can be performed and reported. In a situation where a medical procedure was already performed but the corresponding quality measure code was not entered into a patient's data record, the medical staff can enter the quality measure code to the demographics dataset. When there are no inconsistencies between the specified data records and the reporting requirements, a claim form or an electronic billing transmission can be generated for submission to an insurance provider.

In this way, the quality performance module 22 contains a knowledge-based process for the medical service provider 80 to manage the quality of care provided to patients and ensure that the reportable quality measure information is performed, entered into the patients' data records and reported to the patients' insurance providers. In one embodiment of the invention, the quality performance module 22 can be implemented using object or component software, such as ActiveX, in a practice management system. In such an implementation, the quality performance module 22 contains the algorithms 40 for performing the evaluation 44 and receives a data file with the information needed for the denominator determination 54 and the numerator determination 56.

Figure 5:
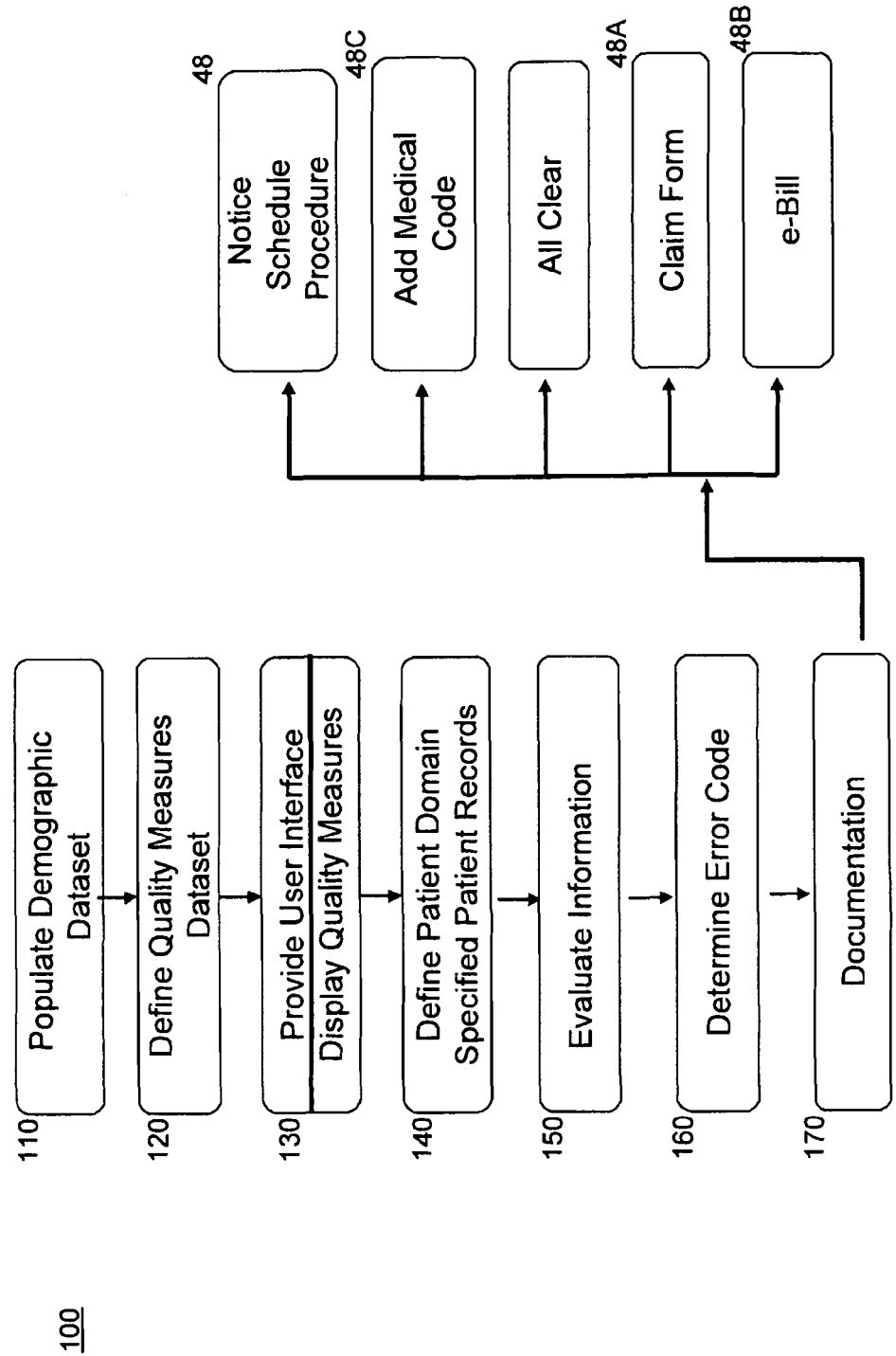
FIG. 5 is a diagram of a practice management system process according to the present invention.

The overall system process 100 is illustrated in the flow chart of FIG. 5. As discussed above with regard to the system, the demographic dataset 12 is populated with the data records 26 for the patients (110), and the quality measure dataset 14 defines the various denominator populations (120). The user interface 16 is in operable communication with the demographics dataset 12 and the quality measure dataset 14 and displays the quality measure identifiers on the selection screen (130). The user selects a quality measure, and the practice management module or the quality measure module uses a logical routine 46 to determine the reportable quality measure codes and specified patient records (140). The quality measure module identifies and evaluates the denominator population for the numerator match (150) and produces the quality measure error code for each data record which does not have the numerator match (160). Based on the quality measure error code, a notice or other documentation is provided to the medical staff (170). As discussed above, a mandated quality measure code may be added to a data record corresponding to the error code, or a patient can be scheduled for a mandated medical procedure so that the quality measure code can be entered properly.

Figure 6B:
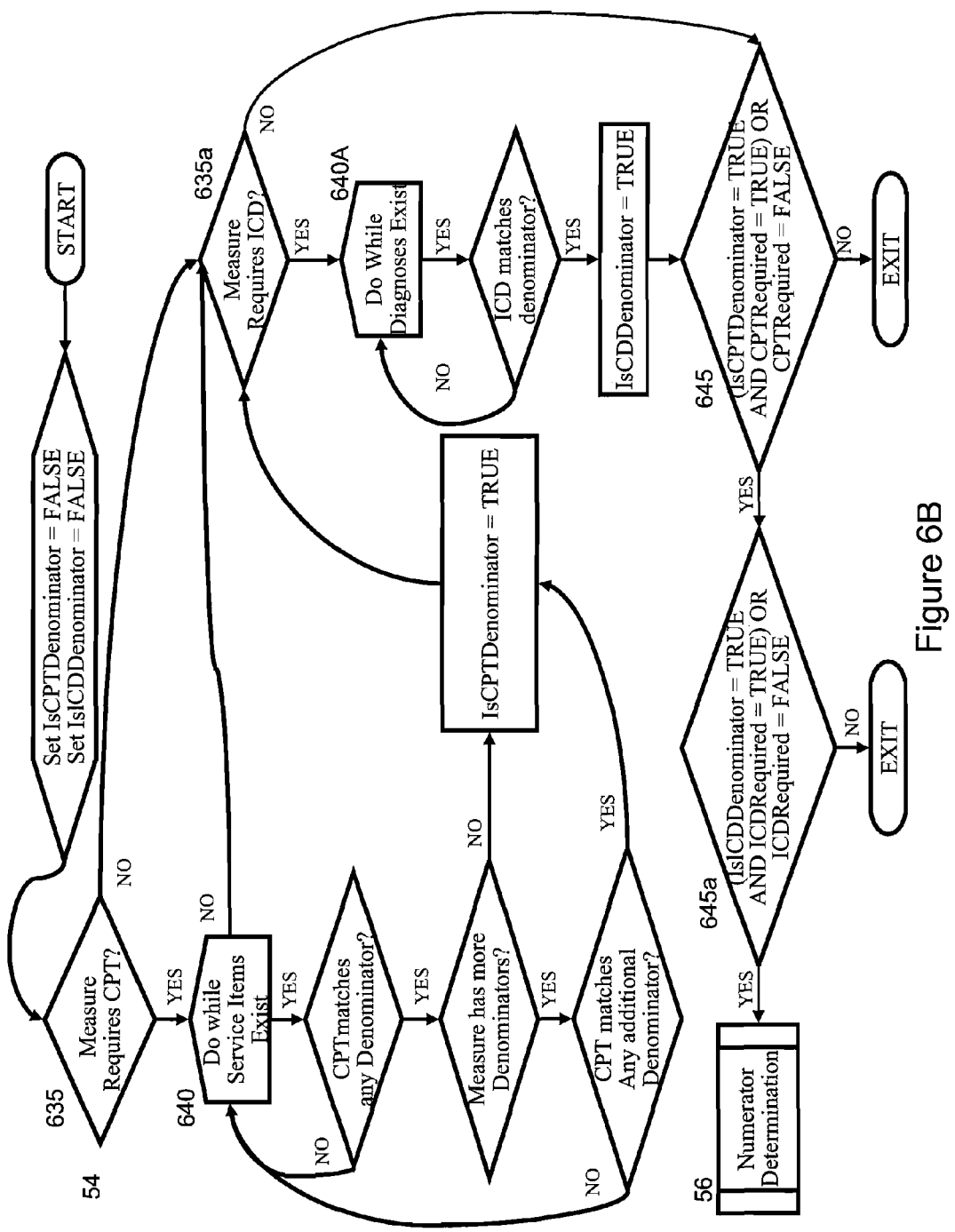
Figure 6C:
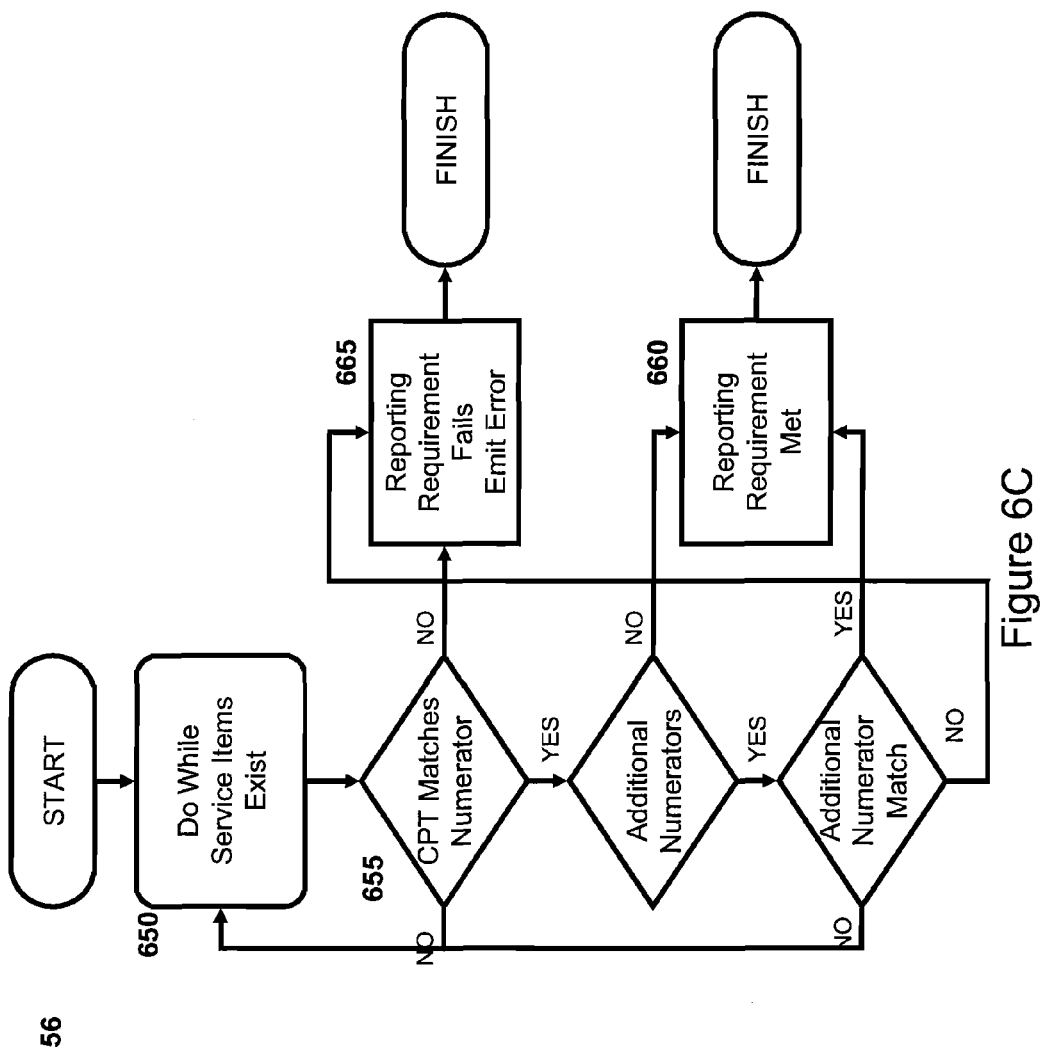

Examples of the logical routine 46 for the quality measure/specified data records selection and the algorithms 40 for the denominator determination 54 and numerator determination 56 are shown according to particular process operations in FIGS. 6A, 6B and 6C, respectively. The YES-path out of the measure determination decision block 605 corresponds with the selection of the defined quality measure identifier, and the system sets the particular quality measure to be evaluated 610. The data records and quality measure requirements for the evaluation is obtained from the demographics dataset and the quality measure dataset 615, respectively. For each of the records, the system determines whether the quality measure information has already been reported or is otherwise retired based on the dates in the records 620. The age and sex determination blocks 620, 625 show the matching of patients' biographical information with specification criteria to identify those data records 26 for the specified data records 36 that are used for the denominator determination 54. As indicated in the EXIT blocks, those records which do not match the specification criteria for the particular quality measure are not passed through to the denominator determination.

In the denominator determination 54, each record is checked for possible exclusion from the denominator population 54A for the particular quality measure. As shown in the "Denominator Coding" of Tables I & II, the CMS PQRI system can define a denominator based on a CPT code (for a medical procedure/service item) and/or an ICD code (for a diagnosis) which are generally described above as a medical condition code. Accordingly, each record is checked for those medical condition codes (CPT &/or ICD) 635, 635A which are defined by the quality measure's denominator requirements, i.e., the medical condition criteria 38A, and the logical routines provide for the looping of multiple records 640, 640A according to the quality measure's denominator requirements, ("Service Items" and/or "Diagnoses"). As shown in the CPT and ICD decision blocks 645, 645A, each record which contains the medical condition code(s) defined by the medical condition criteria 38A in the particular quality measure is then included in the denominator population 54A and communicated to the numerator determination 56. As indicated by the EXIT blocks, there is no need to perform a numerator determination for those records which do not qualify for the denominator population.

In the numerator determination 56, each one of the records in the denominator population 54A is checked for one or more quality measure codes which match any one of the reportable quality measure codes 655 (CPT Category II codes in the CMS PQRI system). As with the denominator determination 54, the logical routines provide for the looping of multiple records 650. If the numerator match is satisfied for all records in the denominator population, the logical routine determines that the reporting requirement is met 660. For each record in which there is not a numerator match, the logical routine determines that the reporting requirement fails 665. For the record(s) in which the reporting requirement fails, the quality reporting module returns the quality measure error code.

It will be appreciated multiple quality measures may be tracked by the system and that data records for some patients may qualify for reporting according to multiple quality measures, such as the measures listed in Tables I & II below. Although the logical routines described above would be followed in a sequential manner for multiple quality measures being evaluated, it is also anticipated that logical routines for multiple quality measures could be evaluated in parallel, preferably by using matrices.

TABLE I

Measure #1: Hemoglobin A1c Poor Control in Type 1 or 2 Diabetes Mellitus

DESCRIPTION:
   Percentage of patients aged 18-75 years with diabetes (type 1 or type 2) who had most recent hemoglobin A1c greater than 9.0%
INSTRUCTIONS :
   This measure is to be reported a minimum of once per reporting period for patients seen during the reporting period. The performance period for this measure is 12 months. It is anticipated that clinicians who provide services for the primary management of diabetes mellitus will submit this measure.
This measure can be reported using CPT Category II codes:
   ICD-9 diagnosis codes, CPT E/M (Evaluation/Management) service codes, and patient demographics (age, gender, etc) are used to identify patients who are included in the measure's denominator. CPT Category II codes are used to report the numerator of the measure.
   When reporting the measure, submit the listed ICD-9 diagnosis codes, CPT E/M service codes, and the appropriate CPT Category II code OR the CPT Category II code with the modifier. The modifier allowed for this measure is: 8P— reasons not otherwise specified. There are no allowable performance exclusions for this measure.
NUMERATOR:
   Patients with most recent hemoglobin A1c level >9.0%
   Numerator Instructions: This is a poor control measure. A lower rate indicates better performance (e.g., low rates of poor control indicate better care)
   Numerator Coding:
   Most Recent Hemoglobin A1c Performed
   CPT II 3046F: Most recent hemoglobin A1c level >9.0%
   OR
   CPT II 3044F: Most recent hemoglobin A1c level <7.0%
   OR
   CPT II 3045F: Most recent hemoglobin A1c level 7.0% to 9.0%
   OR
   Hemoglobin A1c not Performed, Reason Not Specified
   Append a reporting modifier (8P) to CPT Category II code 3046F to report circumstances when the action described in the numerator is not performed and the reason is not otherwise specified.

TABLE I-continued

Measure #1: Hemoglobin A1c Poor Control in Type 1 or 2 Diabetes Mellitus

3 As of: Mar. 29, 2007
8P: Hemoglobin A1c level was not performed during the performance period (12 months), reason not otherwise specified
DENOMINATOR:
  Patients aged 18-75 years with the diagnosis of diabetes
  Denominator Coding:
  An ICD-9 diagnosis code for diabetes and a CPT E/M service code are required to identify patients for denominator inclusion.
  ICD-9 diagnosis codes: 250.00-250.93 (DM), 648.00-648.04 (DM in pregnancy, not gestational)
  AND
  CPT E/M service codes: 99201-99205, 99211-99215 (E/M); 99341-99345, 99347-99350 (home visit); 99304-99310 (nursing facility); 99324-99328, 99334-99337 (domiciliary); G0344
RATIONALE:
  Intensive therapy of glycosylated hemoglobin (A1c) reduces the risk of microvascular complications.
CLINICAL RECOMMENDATION STATEMENTS:
  A glycosylated hemoglobin should be performed during an initial assessment and during follow-up assessments, which should occur at no longer than three-month intervals. (AACE/ACE)
  The A1c should be universally adopted as the primary method of assessment of glycemic control. On the basis of data from multiple interventional trials, the target for attainment of glycemic control should be A1c values ≦6.5%. (AACE/ACE)
  Obtain a glycosylated hemoglobin during an initial assessment and then routinely as part of continuing care. In the absence of well-controlled studies that suggest a definite testing protocol, expert opinion recommends glycosylated hemoglobin be obtained at least twice a year in patients who are meeting treatment goals and who have stable glycemic control and more frequently (quarterly assessment) in patients whose therapy was changed or who are not meeting glycemic goals. (Level of evidence: E) (ADA)
  Because different assays can give varying glycated hemoglobin values, the ADA recommends that laboratories only use assay methods that are certified as traceable to the Diabetes Control and Complications Trial A1c reference method. The ADA's goal for glycemic control is A1c <7%. (Level of evidence: B) (ADA)
  Monitor and treat hyperglycemia, with a target A1C of 7%, but less stringent goals for therapy may be appropriate once patient preferences, diabetes severity, life expectancy and functional status have been considered. (AGS)

TABLE 2

Measure #2: Low Density Lipoprotein Control in Type 1 or 2 Diabetes Mellitus

DESCRIPTION:
  Percentage of patients aged 18-75 years with diabetes (type 1 or type 2) who had most recent LDL-C level in control (less than 100 mg/dl)
INSTRUCTIONS:
  This measure is to be reported a minimum of once per reporting period for patients seen during the reporting period. The performance period for this measure is 12 months. It is anticipated that clinicians who provide services for the primary management of diabetes mellitus will submit this measure.
  This measure can be reported using CPT Category II codes:
  ICD-9 diagnosis codes, CPT E/M service codes, and patient demographics (age, gender, etc) are used to identify patients who are included in the measure's denominator. CPT Category II codes are used to report the numerator of the measure.
  When reporting the measure, submit the listed ICD-9 diagnosis codes, CPT E/M service codes, and the appropriate CPT Category II code OR the CPT Category II code with the modifier. The modifiers allowed for this measure are: 1P— medical reasons, 8P— reasons not otherwise specified.
NUMERATOR:
  Patients with most recent LDL-C <100 mg/dL
  Numerator Coding:
  Most Recent LDL-C Performed
  CPT II 3048F: Most recent LDL-C <100 mg/dL
  OR
  CPT II 3049F: Most recent LDL-C 100-129 mg/dL
  OR
  CPT II 3050F: Most recent LDL-C ≧130 mg/dL
  OR
  LDL-C Level not Performed for Medical Reasons
  Append a modifier (1P) to CPT Category II code 3048F or 3049F or 3050F to report documented circumstances that appropriately exclude patients from the denominator.
  1P: Documentation of medical reason(s) for not performing LDL-C level during the performance period (12 months)
  OR
  LDL-C Level not Performed, Reason Not Specified
  Append a reporting modifier (8P) to CPT Category II code 3048F to report

TABLE 2-continued

Measure #2: Low Density Lipoprotein Control in Type 1 or 2 Diabetes Mellitus circumstances when the action described in the numerator is not performed and the reason is not otherwise specified.
    8P: LDL-C was not performed during the performance period (12 months), reason not otherwise specified
DENOMINATOR:
    Patients aged 18-75 years with the diagnosis of diabetes
    Denominator Coding:
    An ICD-9 diagnosis code for diabetes and a CPT E/M service code are required to
identify patients for denominator inclusion.
    ICD-9 diagnosis codes: 250.00-250.93 (DM), 648.00-648.04 (DM in pregnancy, not
gestational)
    AND
    CPT E/M service codes: 99201-99205, 99211-99215 (E/M); 99341-99345, 99347-99350
(home visit); 99304-99310 (nursing facility); 99324-99328, 99334-99337 (domiciliary), G0344
RATIONALE:
    Persons with diabetes are at increased risk for coronary heart disease (CHD). Lowering
serum cholesterol levels can reduce the risk for CHD events.
CLINICAL RECOMMENDATION STATEMENTS:
    A fasting lipid profile should be obtained during an initial assessment, each follow-up
assessment, and annually as part of the cardiac-cerebrovascular-peripheral vascular module.
(AACE/ACE)
    A fasting lipid profile should be obtained as part of an initial assessment. Adult patients
with diabetes should be tested annually for lipid disorders with fasting serum cholesterol,
triglycerides, HDL cholesterol, and calculated LDL cholesterol measurements. If values fall in
lower-risk levels, assessments may be repeated every two years. (Level of evidence: E) (ADA)
    Patients who do not achieve lipid goals with lifestyle modifications require
pharmacological therapy. Lowering LDL cholesterol with a statin is associated with a reduction
in cardiovascular events. (Level of evidence: A)
    Lipid-lowering therapy should be used for secondary prevention of cardiovascular
mortality and morbidity for all patients with known coronary artery disease and type 2 diabetes.
(ACP)
    Statins should be used for primary prevention against macrovascular complications in
patients with type 2 diabetes and other cardiovascular risk factors.
    Once lipid-lowering therapy is initiated, patients with type 2 diabetes mellitus should be
taking at least moderate doses of a statin.
    Older persons with diabetes are likely to benefit greatly from cardiovascular risk
reduction, therefore monitor and treat hypertension and dyslipidemias. (AGS)

Figure 7:
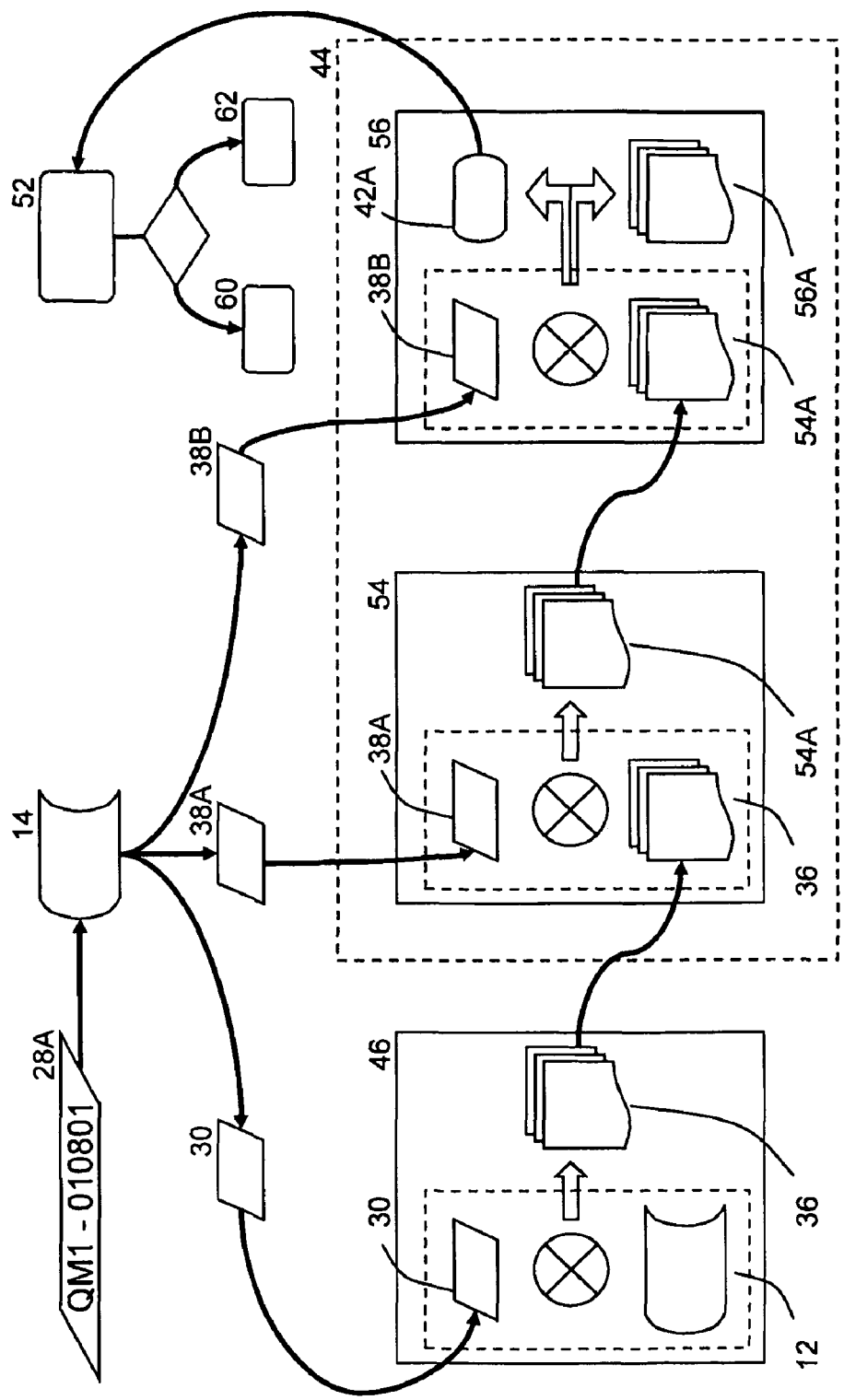
FIG. 7 is a block diagram of the process operations.

In FIG. 7, a path through the system is shown for a set of data records being evaluated by the process described above. A defined quality measure identifier 28A is used to select the particular specification criteria 30, medical condition criteria 38A and reportable quality measure codes 38B from the quality measure dataset 14 for the defined quality measure, such as Quality Measure 1 in Table I above (CMS PQRI ID No. 010801). The logical routine 46 cross-references the specification criteria 30 with the data records 26 in the demographics dataset to determine the specified data records 36. The specified data records 36 are evaluated in denominator determination 54, and those specified data records 36 which include medical condition codes 26D that are equivalent to the medical condition criteria 38A are included in the denominator population 54A. The records in the denominator population 54A are evaluated in numerator determination 56 for numerator matches 56A or lack thereof; for each of the records in the denominator population 54A, the quality measure codes 26E are checked for one or more of the reportable quality measure codes 38B for the particular quality measure. Any record without a match is given a quality measure error code 42A which corresponds with one or more of the corrective actions 52 described above. For corrective actions, the program prompts the user to evaluate the patient's condition and/or chart documentation to determine whether appropriate data exists or whether tests, medications or other diagnostics/treatments should be ordered. The information and options displayed to the user are specific to the information that has been previously obtained for each particular patient.

As particularly shown in the attached screen shots of FIG. 4, a set-up screen displays the measures that may be required in particular situations for a particular patient. For example, the procedures associated with Measure #2 (Low Density Lipoprotein Control in Type 1 or 2 Diabetes Mellitus) may be required for any Medicare patient who is aged 18-75 years with diabetes and who also had most recent LDL-C level in control. The automated system compares particular patient information with the database information for all of the potential measurement criteria, and determines the patient qualifies for reporting on Claim ID Nos. 1101, 1102 and 1103 such as the fictitious patient, Ronald Watson. Accordingly, such a positive identification of patient qualifications with reporting requirements would be included in the denominator of the corresponding measurements and would alert the medical professionals to the need for actions and reporting so that the patient could also be included in the numerator.

In the first report associated with Ronald Watson, the automated system identifies the actions for reporting requirements that have not been met and need to be taken and corresponding reporting required under Claim ID Nos. 1101, 1102 and 1103. Similarly, in the second report associated with Ronald Watson, the automated system indicates the appropriate code that satisfies the reporting requirements. However, the system continues to indicate that the reporting requirements have not yet been met because the NPI information has not been provided for the particular services provided. Accordingly, the system user can enter this information into the record to satisfy the reporting requirements.

It will be appreciated that different insurance providers may have different reporting requirements which may require different algorithms and/or logical routines. For example, if the CMS PQRI system's reporting requirements are further refined by Blue Shield, Tricare, or other commercial insurance providers 84 to require quantifying or otherwise tracking those patients defined by Measure #1 above (Table I) who have their most recent hemoglobin A1c level>9.0%, additional logic would be required to provide the required data. Accordingly, although the particular algorithms and logical routines for the present invention are described relative to the rules of the CMS PQRI system, different or additional rules could result in different or additional algorithms and/or logical routines. In addition to the numerator and denominator rules as exemplified in Tables I and II, the CMS PQRI system has other rules as well, as listed in Table III below.

TABLE III

CMS PQRI Rules

Participation in PQRI is up to the individual provider. One or more providers in a group practice may elect to participate or all providers may elect to participate.

Providers who elect to participate must be using their individual National Provider Identifier (NPI) for claims filing.

Providers are not required to report on all of the measures. Providers may select the measures they wish to report on based on their patient population, specialty and medical practice.

PQRI reporting requires the use of various CPT Category II codes and G codes along with specific PQRI modifiers.

To qualify for a bonus payment on the measures on which a medical service provider elects to report, CMS requires meeting a threshold requirement on quality reporting for the claims associated with the measure. For example, for a 1.5% bonus payment, the quality reporting must be present on at least 80% of the claims for which the clinical indicators, patient demographics and service rendered meet the measure's specifications. Failure to meet the threshold requirement jeopardizes the bonus payment.

Medicare's claims processing systems will treat previously submitted claims that are resubmitted only to add PQRI quality-data codes, as duplicate claims. These claims will not be included in the PQRI analysis.

To assist with correct usage of PQRI reporting codes and to identify claims that qualify for PQRI reporting but on which PQRI measure codes are missing, the automated process of the present invention was developed specifically in response to the PQRI requirements. However, it should be appreciated that the automatic processes used for these PQRI requirements can also be used for other insurance providers, such as Blue Shield, Tricare, and commercial insurance companies that may develop their own rules and requirements.

The present invention is design to encompass updates to performance measurement programs as they grow in size and scope, including the government programs, such as CMS PQRI, as well as programs instituted by private insurance carriers. For example, data for new programs can be added to the system. Accordingly, the invention can keep track of multiple quality reporting programs and appropriately report to the user based of the insurance carrier involved, their individual program's data requirements and which programs the provider chose or was required to participate in. Future quality performance measures may also require additional tracking criteria which can be included in the system.

Selection of Measurement Criteria: Each measure is able to be selectively enabled for specific PQRI measures that a medical service provider may choose to report. For enabled PQRI measures, each claim is evaluated for potential PQRI reporting requirements based on the patient demographics, clinical conditions and services rendered. If the PQRI reporting is missing or is incorrect based on the CPT II or G-codes used, an edit message is displayed to the system user for the claim.

Validation of Provider's NPI: Since PQRI reporting requires the use of the provider's individual NPI, the present invention confirms the existence of a correctly formatted NPI on potential PQRI claims. In the event that a correctly formatted NPI is not provided on potential PQRI claims, a missing NPI error message is reported to the system user.

Validation of Code Modifiers: PQRI measures may require appending a modifier to a CPT Category II code. The automated system validates the proper use of modifiers on PQRI reporting codes.

Accordingly, the purpose of the present system is to automate the process by which medical service providers cross-reference the service requirements and the reporting requirements that insurance providers respectively place on the diagnosis, testing and treatment of patients, or medical procedures and protocols generally, with specific patient records and the corresponding reporting thereof.

The quality measure codes 26E can quantify particular medical services and outcomes according to a range of quality standards, such as with the CPT Category II codes and may relate to laboratory test results, treatment regimens, including ordered medications, and other medical protocols in testing and treating the patients' medical conditions as well as the patients' particular outcomes from the medical services being provided.

The present invention may be integrated with a number of software packages used in medical practices, such as practice management software for the medical industry, electronic medical/health records software (EMR or EHR), and other software for the medical industry, including claims editing software, claims adjudication software, and electronic claims transmission software (EDI). The present invention helps medical service providers and their staff in their selections of the measures that they wish to report on and tracks the measures that they wish to report on. The present invention also prompts medical service providers to take certain actions: 1. provide appropriate services and order appropriate tests for the quality measures selected to report on; 2. document appropriate services and tests ordered based on the quality measures selected to report on; and 3. ensure appropriate information is included on claim forms or electronic billing transmissions. The prompts can be communicated to the appropriate medical service staff, including persons involved in scheduling appointments, providing the medical care to the patients and ordering tests, and reporting provider services.

Accordingly, the present invention provides a method of displaying all of the reporting measures, allowing a user to select which they wish to participate in and therefore report on. The present invention also provides a method to gather data from other software applications, including the types listed above as well as other software programs. The invention provides algorithms that after gathering the appropriate data on diagnoses, procedures, age and sex, evaluates the appropriateness of including the information into the reporting of quality measures. The invention's algorithm evaluates whether all the code data currently exist to correctly report a quality measure, if all criteria already exist it passes with no prompts. If all data needed to correctly report the quality measure does not already exist, it would then prompt the system user to take appropriate action to ensure the quality measure is met. The appropriate action to take would depend on the particular user of the software, the application into which the system is integrated and where the patient encounter is, in the workflow process. Differences in actions based on the integration of the system are exemplified with two (2) situations. When the invention is integrated into an EMR, a physician can be alerted to order a specific test needed to comply with the quality measure. When the invention is integrated into a Practice Management, Claims Editing or EDI Software program, a medical coder can be prompted to code out appropriate Category II codes and or appropriate modifiers.

It will be appreciated that the present invention can be used throughout the entire medical service process, from patient intake with office staff, through patient testing, diagnosis, and treatment with the physician, nurse, physician assistant or other medical service provider, and on to patient follow up and reporting obligations to the insurance provider. As discussed above, the denominator population is defined by codes specified in the measure that are submitted as part of a claim and is automatically determined as set forth in the attached flow charts. Similarly, to successfully report quality data for a measure under the insurance programs, such as the PQRI program, a numerator code should be reported and the numerator algorithm of the present invention correlates the actions to be performed with the instructions specific to each measure, including instructions for some measures that may limit the frequency of the reporting requirements, as shown in the attached flow charts. The invention does not need to prompt the system user when no data exist indicating a patient might qualify for a quality measure that the provider had chosen to report on.

The invention can capture data indicating that all coding and transmitting of data needed to satisfy reporting on an individual patient for any reporting year was completed and as such would not continue prompting a user to report unnecessary data.

As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. A system for managing the care of patients and the reporting of the care by medical service providers to the patients' insurance providers, comprising:
    a demographics dataset stored in a database for the patients comprising data records on age, gender, and at least one medical condition code for each of the patients, said data records further comprising a plurality of quality measure codes with corresponding dates for each of the patients;
    a quality measure dataset stored in said database comprising a plurality of quality measure identifiers and corresponding sets of specification criteria, medical condition criteria and reportable quality measure codes, wherein said specification criteria are comprised of an age criteria and a gender criteria;
    a user interface in operable communication with said demographics dataset and said quality measure dataset, wherein said user interface comprises a plurality of patient information data fields, a selection screen listing said quality measure identifiers;
    a computer processor in operative communication with said demographics dataset, said quality measure dataset and said user interface, said computer processor comprising logical means that perform functions for selecting specified data records from said demographic dataset according to a defined quality measure identifier, wherein said defined quality measure identifier is selected from said quality measure identifiers through said user interface and correlates with a unique combination of said specification criteria and said reportable quality measure codes;
    a quality performance module comprising a set of algorithms and a set of error codes, wherein said error codes correspond to a set of corrective actions for the medical service providers, said quality performance module receiving said specified data records, performing an evaluation of said specified data records with said set of algorithms and determining a quality measure error code from said set of error codes according to said evaluation before said specified data records are submitted to the insurance providers, wherein said quality measure error code comprises a notification indicating a reporting requirement has not been met and further comprising a plurality of allowed reporting codes that satisfy said reporting requirement; and
    a reporting module in operable communication with said quality performance module and said user interface, wherein said reporting module creates insurance claim documentation for submission to at least one of the insurance providers, wherein said reporting module further creates a notice with said quality measure error code communicated to said user interface, wherein said notice is created before said insurance claim documentation is submitted to one of the insurance providers, wherein one of said allowed reporting codes corresponds to a reporting requirement correction that is made through said user interface to at least one data record in said claim documentation and wherein said reporting requirement correction resolves said quality measure error code for said data record before said insurance claim documentation is submitted to one of the insurance providers.

2. The system as set forth in claim 1, wherein said quality performance module determines a first set of said allowed medical codes corresponding with a first quality measure error code related to a first quality measure condition and said medical condition code and further displays a second set of said allowed medical codes corresponding with a second quality measure error code related to a second quality measure condition and said medical condition code.

3. The system as set forth in claim 1, wherein said quality performance module determines a plurality of quality measure error codes for an unmet reporting requirement corresponding with said medical condition code, wherein each of said quality measure error codes comprises a text notification indicating a reporting requirement has not been met and further comprises a set of said allowed reporting codes that satisfy said reporting requirement, wherein one of said quality measure error codes in one set corresponds with a first quality measure condition and wherein another of said quality measure error codes in another set corresponds with a second quality measure condition, wherein said first quality measure condition and said second quality measure condition are alternative patient conditions relating to said medical condition code.

4. The system as set forth in claim 1, wherein said quality measure dataset further comprises a flag for identifying said defined quality measure identifier and wherein said quality measure error code corresponds to a corrective action selected from the group consisting of a scheduling warning and a reporting warning.

5. The system as set forth in claim 1, wherein said data records in said demographics dataset further comprise insurance provider information for each of the patients, wherein said quality measure dataset further comprises a first set of specification criteria for a first insurance provider and a second set of specification criteria for a second insurance provider, and wherein said quality performance module further comprises a first set of algorithms for said first insurance provider and a second set of algorithms for said second insurance provider, and wherein said set of algorithms is comprised of a denominator determination and a numerator determination.

6. The system as set forth in claim 5, wherein said denominator determination is comprised of a selection of said specified data records having a medical condition code corresponding with said medical condition criteria for a denominator population, wherein said numerator determination is comprised of a plurality of matches between said reportable quality measure codes and said quality measure codes in said specified data records of said denominator population, and wherein said quality measure error code corresponds with each of said specified data records from said denominator population not having one of said matches in said numerator determination.

7. The system as set forth in claim 6, wherein said quality measure dataset further comprises an exclusion identifier, said exclusion identifier defining exclusion criteria for excluding a specified data record from said denominator population, and wherein said specification criteria further comprises a date criteria defining a range of dates for said specified data records.

8. The system as set forth in claim 1, wherein said data records in said demographics dataset further comprise attending physician identifiers and wherein said medical condition codes are comprised of CPT E/M service codes and ICD-9 diagnosis codes and wherein said quality measure codes are comprised of CPT Category II quality service codes, wherein said quality measure dataset further comprises a set of flags for selectively enabling and identifying a set of defined quality measure identifiers for at least one of the medical service providers, and wherein unselected quality measure identifiers may be selectively enabled at a later time.

9. The system as set forth in claim 1, wherein said reporting requirement correction is added to said demographics dataset through said patient information data fields of said user interface according to said quality measure error code.

10. The system as set forth in claim 1, further comprising a practice management module and a scheduling module, wherein said practice management module is in operable communication with said demographics dataset, said user interface and said quality performance module, said practice management module further comprising said logical means, and, wherein a mandated medical procedure is entered into said scheduling module through said user interface according to said quality measure error code.

11. An improved patient care management system implemented by a computer processor wherein a reporting module retrieves data records from a demographics dataset stored in a database for patients of a medical service provider and creates billing support documentation that is submitted to the insurance providers of the patients, wherein the data records comprise information on age, gender, medical condition codes and quality measure codes, the improvement comprising:
  a quality measure dataset stored in the database comprising a quality measure identifier, wherein said quality measure identifier defines a plurality of data records for a denominator population in said demographics dataset and a set of corresponding reportable quality measure codes;
  a user interface in operable communication with said quality measure dataset and comprising a selection screen listing said quality measure identifier, wherein a selection of a quality measure identifies corresponds with a defined medical condition code from the medical condition codes in the data records; and
  a quality performance module in operable communication with said user interface and comprising a logical means in the computer processor for identifying a numerator match between said set of corresponding reportable quality measure codes and said quality measure codes in each of said data records of said denominator population and a quality measure error code for a data record not having said numerator match, wherein said quality measure error code comprises a text notification indicating a reporting requirement has not been met for said defined medical condition code and further comprising a plurality of allowed reporting codes that satisfy said reporting requirement for said selected medical condition code.

12. The system as set forth in claim 11, wherein said quality performance module determines a plurality of quality measure error codes for an unmet reporting requirement corresponding with said defined medical condition code, wherein each of said quality measure error codes comprises said text notification and further comprises a set of said allowed reporting codes that satisfy said reporting requirement, wherein one of said quality measure error codes corresponds with a first quality measure condition and a first set of allowed reporting codes and wherein another of said quality measure error codes corresponds with a second quality measure condition and a second set of allowed reporting codes, wherein said first quality measure condition and said second quality measure condition are alternative patient conditions relating to said defined medical condition code.

13. The system as set forth in claim 12, wherein said quality measure dataset further comprises a flag for identifying said quality measure identifier, a first set of specification criteria for a first insurance provider and a second set of specification criteria for a second insurance provider and wherein said medical condition codes are comprised of CPT E/M service codes and ICD-9 diagnosis codes and wherein said quality measure codes are comprised of CPT Category II quality service codes, wherein said quality measure dataset further comprises a set of flags for selectively enabling and identifying a set of defined quality measure identifiers for at least one of the medical service providers, wherein unselected quality measure identifiers may be selectively enabled at a later time, and wherein said quality measure error code corresponds to a corrective action selected from the group consisting of a scheduling warning and a reporting warning.

14. The system as set forth in claim 12, wherein said defined medical condition code is an indicator of diabetes and said first set of allowed reporting codes are correlated to a patient having a most-recent hemoglobin A1c with poor control and wherein said second set of allowed reporting codes are correlated to a patient having a most recent LDL-C level in control.

15. The system as set forth in claim 11, further comprising a practice management module, said practice management module comprising a logical means in the computer processor for tracking medical care being provided to the patients by the medical service provider, wherein one of said allowed reporting codes is selected through said user interface as a reporting requirement correction and said reporting requirement correction is added to the data records in the demographics dataset to resolve said quality measure error code before reporting the data records to the insurance providers.

16. The system as set forth in claim 15, further comprising a scheduling module, wherein said quality measure error code corresponds to a scheduling warning, and wherein a mandated medical procedure is entered into said scheduling module according to said quality measure error code.

17. A method for managing the care of patients and the reporting of the care to the patients' insurance providers, comprising the steps of:
  populating a database with a demographic dataset for a plurality of patients, wherein said demographic dataset comprises data records with age, gender, at least one medical condition code, and a plurality of quality measure codes with corresponding dates;
  defining a plurality of denominator populations with a quality measure dataset, wherein said quality measure dataset comprises a plurality of quality measure identifiers and sets of specification criteria and corresponding medical condition criteria and reportable quality measure codes, and wherein said specification criteria are comprised of an age criteria, a gender criteria and a date criteria;
  providing a computer processor with a user interface in operable communication with said demographics dataset and said quality measure dataset, wherein said user interface comprises a plurality of patient information data fields and a selection screen on a display device;
  displaying said quality measure identifiers on said selection screen;
  selecting a quality measure from said quality measure identifiers displayed on said selection screen with said user interface, wherein said selected quality measure correlates with a unique combination of specification criteria and a defined set of corresponding medical condition criteria and reportable quality measure codes;
  identifying data records in said demographic dataset fitting into a denominator population according to said specification criteria and said medical condition criteria;
  evaluating each of said data records in said denominator population in a quality performance module of said computer processor for a match between said reportable quality measure codes and said quality measure codes in said data records;
  producing a quality measure error code with an algorithm in said computer processor for a data record not having said match before submitting said data records to one of the insurance providers, wherein said quality measure error code comprises a notification indicating a reporting requirement has not been met for said selected quality measure and further comprising a plurality of allowed reporting codes that satisfy said reporting requirement for said unmatched data record; and
  displaying a notice using said user interface showing said notification and said allowed reporting codes, wherein one of said allowed reporting codes corresponds to a reporting requirement correction that is made through said user interface to said unmatched data record and wherein said reporting requirement correction resolves said quality measure error code for said unmatched data record.

18. The method according to claim 17, further comprising the step of entering reporting requirement correction into said unmatched data record before submitting said data records to one of the insurance providers.

19. The method according to claim 18, wherein one of said quality measure error codes corresponds with a first quality measure condition and a first set of allowed reporting codes and wherein another of said quality measure error codes corresponds with a second quality measure condition and a second set of allowed reporting codes, wherein said first quality measure condition and said second quality measure condition are alternative patient conditions relating to said medical condition code.

20. The method according to claim 19, further comprising the step of displaying details on said medical condition code as an indicator of diabetes, wherein said first set of allowed reporting codes are correlated to a patient having a most-recent hemoglobin A1c with poor control and wherein said second set of allowed reporting codes are correlated to a patient having a most recent LDL-C level in control.

* * * * *